US008419832B2

(12) United States Patent
Capdeville et al.

(10) Patent No.: US 8,419,832 B2
(45) Date of Patent: Apr. 16, 2013

(54) PROCESS FOR THE PURIFICATION OF GASEOUS MIXTURES CONTAINING MERCAPTANS AND OTHER ACID GASES (75) Inventors: Serge Capdeville, Poey de Lescar (FR); Jean-Louis Peytavy, Lescar (FR); Georges Fremy, Sauveterre de Bearn (FR); Didier Anglerot, Lons (FR)

(73) Assignee: Total S.A., Courbevoie (FR)

( * ) Notice: Subject to any disclaimer, the term of this patent is extended or adjusted under 35 U.S.C. 154(b) by 847 days.

(21) Appl. No.: 12/161,010

(22) PCT Filed: Jan. 16, 2007

(86) PCT No.: PCT/FR2007/000073
§ 371 (c)(1),
(2), (4) Date: Jan. 5, 2009

(87) PCT Pub. No.: WO2007/083012
PCT Pub. Date: Jul. 26, 2007

(65) Prior Publication Data
US 2010/0154637 A1 Jun. 24, 2010

(30) Foreign Application Priority Data
Jan. 18, 2006 (FR) ...................................... 06 00448

(51) Int. Cl.
B01D 53/14 (2006.01)

(52) U.S. Cl.
USPC ............... 95/235; 95/236; 423/228; 423/229; 423/242.7

(58) Field of Classification Search .................... 95/174; 236/235, 236; 423/228, 229, 242.7; 252/60
See application file for complete search history.

(56) References Cited

U.S. PATENT DOCUMENTS

| 2,881,047 | A | * | 4/1959 | Townsend ..................... 423/222 |
| 5,589,149 | A |  | 12/1996 | Garland |
| 5,705,090 | A |  | 1/1998 | Garland |
| 6,277,345 | B1 |  | 8/2001 | Stankowiak |
| 7,419,646 | B2 | * | 9/2008 | Cadours et al. ............... 423/220 |
| 7,666,813 | B2 | * | 2/2010 | Hoefer et al. ................. 502/401 |
| 8,287,626 | B2 | * | 10/2012 | Hoang-Dinh et al. .......... 95/174 |
| 2005/0202967 | A1 | * | 9/2005 | Hoefer et al. ................. 502/401 |

FOREIGN PATENT DOCUMENTS
WO  PCT/US2004/007453  10/2004

* cited by examiner

Primary Examiner — Duane Smith
(74) Attorney, Agent, or Firm — Juan J. Lizarraga (57) ABSTRACT The invention relates to a process for the purification of a gaseous mixture containing mercaptans and other acid gases comprising a stage of bringing said gaseous mixture into contact with an absorbent solution comprising an alkanolamine, a $C_2$-$C_4$ thioalkanol and water.

38 Claims, 5 Drawing Sheets

PROCESS FOR THE PURIFICATION OF GASEOUS MIXTURES CONTAINING MERCAPTANS AND OTHER ACID GASES

FIELD OF THE INVENTION

The present invention relates to a process for the purification of gaseous mixtures, in particular of natural gas, containing mercaptans and other acid gases, as well as an absorbent solution for the implementation of said process.

TECHNICAL BACKGROUND

Within the framework of the production of natural gas (containing mainly methane) or liquefied natural gas, it is necessary to purify said natural gas, which originates from a deposit, by removing a certain number of contaminants, including primarily what are called "acid gases", i.e. carbon dioxide ($CO_2$), hydrogen sulphide ($H_2S$), mercaptans (R—SH), carbonyl sulphide (COS) and carbon disulphide ($CS_2$).

Carbon dioxide and hydrogen sulphide can represent a significant part of the gaseous mixture originating from a natural gas deposit, typically from 3 to 70% (in molar concentration). COS is present in smaller quantities, typically varying from 1 to 50 ppm by volume.

The contaminants which have to be removed include mercaptans, molecules of formula R—SH where R is an alkyl group. The total quantity of mercaptans in a gaseous mixture originating from a natural gas production site can represent a few hundred ppm by volume. The main two mercaptans concerned are methyl mercaptan and ethyl mercaptan, but other mercaptans (in particular molecules of type $C_3SH$ to $C_6SH$) can also be present, generally at a lower concentration.

Numerous methods currently exist for deacidifying and removing mercaptans from natural gas (simultaneously or sequentially), using solvents capable of absorbing mercaptans and/or other acid gases chemically and/or physically (by dissolution).

Among the processes currently in use on an industrial scale, the so-called "Sulfinol" process involves eliminating the $H_2S$, $CO_2$, COS, $CS_2$ gases and the natural gas mercaptans using a solvent constituted by a mixture of sulpholane, water and an amine (such as diisopropanolamine or methyl diethanolamine). Another example is the so-called "Selexol" process, which uses a solvent based on a dimethyl ether of polyethylene glycol.

Numerous other variants have been proposed, using alternative solvents. By way of example there can be mentioned solvents based on alkanolpyridine (U.S. Pat. No. 4,360,363).

However, there is still a real need to discover other solvents capable of effectively absorbing, preferably simultaneously, the mercaptans and other acid gases present in a gaseous mixture.

In particular there is a need to discover solvents making it possible to implement processes for the deacidification and demercaptanization of gaseous mixtures with a lower solvent flow rate compared with the state of the art (at a comparable gaseous mixture flow rate), and more generally at a lower cost compared with the state of the art.

SUMMARY OF THE INVENTION

The invention makes it possible to meet the needs expressed above, thanks to the development of a novel hybrid solution constituted by a mixture of alkanolamine, water and thioalkanol, making it possible to effectively co-absorb the mercaptans and the other acid gases contained in a gaseous mixture.

The invention therefore relates primarily to a process for the purification of a gaseous mixture containing acid gases and preferably containing mercaptans and other acid gases comprising a stage of bringing said gaseous mixture into contact with an absorbent solution comprising an alkanolamine, a $C_2$-$C_4$ thioalkanol and water.

Preferably, said gaseous mixture is natural gas.

Preferably, the mercaptan or mercaptans comprise methyl mercaptan and/or ethyl mercaptan.

Preferably, the other acid gas or gases comprise hydrogen sulphide and/or carbon dioxide and/or carbonyl sulphide.

According to an advantageous embodiment, the alkanolamine is diethanolamine.

According to a particular embodiment, the $C_2$-$C_4$ thioalkanol is ethylene dithioethanol.

Advantageously, the $C_2$-$C_4$ thioalkanol is thiodiethylene glycol.

According to a preferred embodiment of the process according to the invention, the absorbent solution comprises:
 approximately 20 to approximately 60% by mass of diethanolamine;
 approximately 20 to approximately 60% by mass of water; and
 approximately 10 to approximately 40% by mass of thiodiethylene glycol.

According to a particularly preferred embodiment of the process according to the invention, the absorbent solution comprises:
 approximately 30 to approximately 45% by mass of diethanolamine;
 approximately 30 to approximately 50% by mass of water; and
 approximately 15 to approximately 30% by mass of thiodiethylene glycol.

According to a most preferred embodiment of the process according to the invention, the absorbent solution comprises:
 approximately 40% by mass of diethanolamine;
 approximately 40% by mass of water; and
 approximately 20% by mass of thiodiethylene glycol.

Preferably, the above-mentioned purification process is implemented in an absorber at a temperature comprised between approximately 40 and approximately 100° C., preferably approximately 50 and approximately 90° C.

Advantageously, in the purification process as defined above, the gaseous mixture is brought into contact with the absorbent solution at a gaseous mixture flow rate comprised between $0.23 \times 10^6$ $Nm^3$/day and $56 \times 10^6$ $Nm^3$/day and at an absorbent solution flow rate comprised between 800 $m^3$/day and 50000 $m^3$/day.

Advantageously, the purification process as defined above moreover comprises a stage of regeneration of the absorbent solution loaded with mercaptans and other acid gases at a regeneration pressure comprised between 0 and 20 bar and preferably between 1 and 2 bar, and at a temperature comprised between 100 and 140° C.

According to a preferred embodiment, the invention relates to the purification process as defined above, for reducing the concentration of mercaptans contained in the gaseous mixture to a value of less than approximately 5 ppm.

According to a preferred embodiment, the invention relates to the purification process as defined above, for reducing the concentration of hydrogen sulphide contained in the gaseous mixture to a value of less than approximately 4 ppm.

According to a preferred embodiment, the invention relates to the purification process as defined above, for reducing the concentration of carbon dioxide contained in the gaseous mixture to a value of less than approximately 50 ppm.

According to a preferred embodiment, the invention relates to the purification process as defined above, for reducing the concentration of carbonyl sulphide contained in the gaseous mixture to a value of less than approximately 1 ppm.

The invention moreover relates to an absorbent solution comprising:
- approximately 20 to approximately 60% by mass of an alkanolamine;
- approximately 20 to approximately 60% by mass of water; and
- approximately 10 to approximately 40% by mass of a $C_2$-$C_4$ thioalkanol.

The absorbent solution according to the invention preferably comprises:
- approximately 30 to approximately 45% by mass of an alkanolamine;
- approximately 30 to approximately 50% by mass of water; and
- approximately 15 to approximately 30% by mass of a $C_2$-$C_4$ thioalkanol.

According to a preferred embodiment of the above-mentioned absorbent solution, the alkanolamine is diethanolamine.

According to a preferred embodiment of the above-mentioned absorbent solution, the $C_2$-$C_4$ thioalkanol is thiodiethylene glycol or ethylene dithioethanol.

BRIEF DESCRIPTION OF THE FIGURES

FIG. 1 represents the result of a comparative pilot test of the absorption of methyl mercaptan contained in a gaseous mixture (on a column), by an absorbent solution according to the invention on the one hand (diethanolamine 40%, water 40% and thiodiethylene glycol 20%) and by a standard absorbent solution on the other hand (diethanolamine 40%, water 40% and sulpholane 20%). The percentage by volume of methyl mercaptan in the gaseous mixture is shown along the x-axis, and the number of plate trays passed through by the gaseous mixture in the column is shown along the y-axis. □: measurements obtained with the standard absorbent solution; ○: measurements obtained with the absorbent solution according to the invention. For each absorbent solution, three tests are carried out, each time with a different initial $CH_3SH$ concentration.

DESCRIPTION OF EMBODIMENTS OF THE INVENTION

The invention is now described in greater detail and non-limitatively in the following description.

Gases to be Treated.

The invention allows the treatment of a gaseous mixture, and in particular according to a preferred embodiment, of natural gas. The latter contains mercaptans, in particular methyl mercaptan and/or ethyl mercaptan, in quantities by volume varying from 0 to 400 ppm.

The gaseous mixture also comprises other acid gases, in particular hydrogen sulphide and/or carbon dioxide and/or carbonyl sulphide, all in quantities by volume of: less than 50% $H_2S$, less than 50% $CO_2$ and between 0 and 100 ppm COS.

Although the invention is particularly useful for treating a gaseous mixture containing mercaptans, it must be noted that the invention is used more generally for the purification of any gaseous mixture containing acid gases, with or without mercaptans. Apart from the field of natural gas treatment, the invention can also be used for example in the treatment of flue gases.

Absorbent Solution.

The invention uses a novel absorption solution, in a standard absorption/regeneration process. The novel solution provides a chemical and physical absorption according to the components to be absorbed.

The absorbent solution according to the invention generally comprises:
- approximately 20 to approximately 60% by mass of an alkanolamine; advantageously approximately 30 to approximately 45%;
- approximately 20 to approximately 60% by mass of water; advantageously approximately 30 to approximately 50% by mass of water; and
- approximately 10 to approximately 40% by mass of a $C_2$-$C_4$ thioalkanol; advantageously approximately 15 to approximately 30%.

A preferred solution comprises the above components in a ratio of 40/40/20.

Diethanolamine (DEA) is the compound of formula $HN(CH_2—CH_2OH)_2$, which is the preferred alkanolamine. Apart from DEA, other examples of alkanolamines which can be used in the process according to the invention include by way of example monoethanolamine (MEA), triethanolamine (TEA), diisopropanolamine (DIPA) and methyl diethanolamine (MDEA), or even activated methyl diethanolamine (for example methyl diethanolamine enriched with hydroxyethyl piperazine or piperazine) or also sterically hindered amines.

Generally, the $C_2$-$C_4$ thioalkanol has the formula R—S—$C_{2-4}$—OH, where R is any group, for example, an alkyl group or an alcohol group or a thiol group or an alkylthioalkanol group, the group containing in particular up to 6 carbon atoms.

According to a particular embodiment, the $C_2$-$C_4$ thioalkanol is a dimeric molecule.

An example of $C_2$-$C_4$ thioalkanol which can be used according to the invention is ethylene dithioethanol, of formula (HO—$CH_2$—$CH_2$)—S—($CH_2$—$CH_2$)—S—($CH_2$—$CH_2$—OH).

Thiodiethylene glycol or thiodiglycol (TDG) is the compound of formula S($CH_2$—$CH_2$—OH)$_2$, which is the preferred thioalkanol. Apart from TDG, other $C_2$-$C_4$ thioalkanols can also be used according to the invention, in particular methyl thioethanol. It is also possible to use a mixture of the above compounds.

The preferred composition of the absorbent solution according to the invention (40% DEA, 40% water and 20% TDG) results from a compromise: in fact the more TDG the absorbent solution contains, the greater the solubility of the $CO_2$ and the mercaptans, which is favourable to the purification of the gaseous mixture; in return, the more TDG the absorbent solution contains, the lower the surface tension of the solution, and the greater the viscosity of the solution, which is unfavourable to the transfer of the mercaptans and other acid gases into the solution. It is to be noted however that the effect on viscosity of an increase in the TDG concentration can be counterbalanced by an increase in temperature, which makes it possible to be free of the viscosifying effect of the thioalkanol.

When another compound, for example ethylene dithioethanol, is used instead of TDG, its preferred concentration is generally the same as that of TDG.

Absorption and Regeneration Process.

The invention uses a standard absorption regeneration process but with a novel absorption solution.

The absorption stage is implemented in an absorber at a temperature comprised between approximately 40 and approximately 100° C., preferably approximately 50 and approximately 90° C.

The pressure in the column is comprised between 1 and 150 bar, preferably between 40 and 100 bar.

As a column, it is possible to use any type of useful column, and in particular a perforated plate tray column, a valve column or a cap column.

The implementation of the absorption is carried out by bringing the gaseous mixture into contact with the absorbent solution at a gaseous mixture flow rate of between $0.23 \times 10^6$ $Nm^3$/day and $56 \times 10^6$ $Nm^3$/day and at an absorbent solution flow rate of between 800 and 50000 $m^3$/day.

As regards the absorbent solution regeneration stage, it is implemented in a standard fashion by heating and separation of the mercaptans and other acid gases absorbed by the solution in a regeneration column. In fact, the amine solution loaded with $H_2S$, $CO_2$ and RSH (so-called rich amine) originating from the bottom of the absorber is sent into an intermediate-pressure flash drum. The gases originating from the flash of the rich amine are used as fuel gases.

The rich amine is then reheated and optionally partially vaporized in an amine/amine exchanger by the hot amine at the bottom of the regenerator, then fed to the regeneration column.

The reboiler generates vapour which rises in counter-current in the column, entraining the acid constituents $H_2S$, $CO_2$ and RSH. This desorption is encouraged by the low pressure and the high temperature prevailing in the regenerator.

At the head of the column, the acid gases are cooled in a condenser. The condensed water is separated from the acid gas in a reflux drum and sent either to the head of the regeneration column, or directly to the lean amine solution tank.

The regenerated amine (also called lean amine) is then recycled to the absorption stage.

It should be noted that a semi-regenerated operating mode can also be envisaged.

The process according to the invention makes it possible to achieve appreciable separation performances, and in particular to reduce the mercaptan concentration to a value of less than approximately 5 ppm, the hydrogen sulphide concentration to a value of less than approximately 4 ppm, the carbon dioxide concentration to a value of less than approximately 50 ppm and the carbonyl sulphide concentration to a value of less than approximately 1 ppm.

The natural gas treated then undergoes a dehydration stage and can then be available for the gas distribution network. It can also undergo cryogenic treatment in order to produce liquefied natural gas.

EXAMPLES

The following examples illustrate the invention without limiting it.

Example 1

Ability of an Absorbent Solution According to the Invention to Scrub Methyl Mercaptan Several pilot tests were carried out on a Koch-Glitsch perforated tray column comprising 11 plate trays. The gas treated in the column contains approximately 12% $CO_2$. The quantity of methyl mercaptan is variable according to the tests.

The parameters are the following:
  for the gaseous mixture: flow of 215 kg/h; total pressure of 40 bars; partial pressure of $CO_2$ 4.8 bars; composition: approximately 88% $N_2$, 12% $CO_2$, 0 to 50 ppm $H_2S$ and 200 to 1200 ppm R—SH.
  for the absorbent solution: flow rate of 1180 kg/h; temperature of 50° C.; $CO_2$ content of 0.1 to 0.3%;
  for the regeneration: pressure of 2.5 to 2.7 bar; feed temperature of 115 to 118° C.; base temperature of 135 to 137° C.; reflux of 40 to 55 kg/h.

Two absorbent solutions are tested:
  a standard absorbent solution, containing 40% DEA, 40% water and 20% sulpholane;
  an absorbent solution according to the invention, containing 40% DEA, 40% water and 20% TDG.

Figure 1:
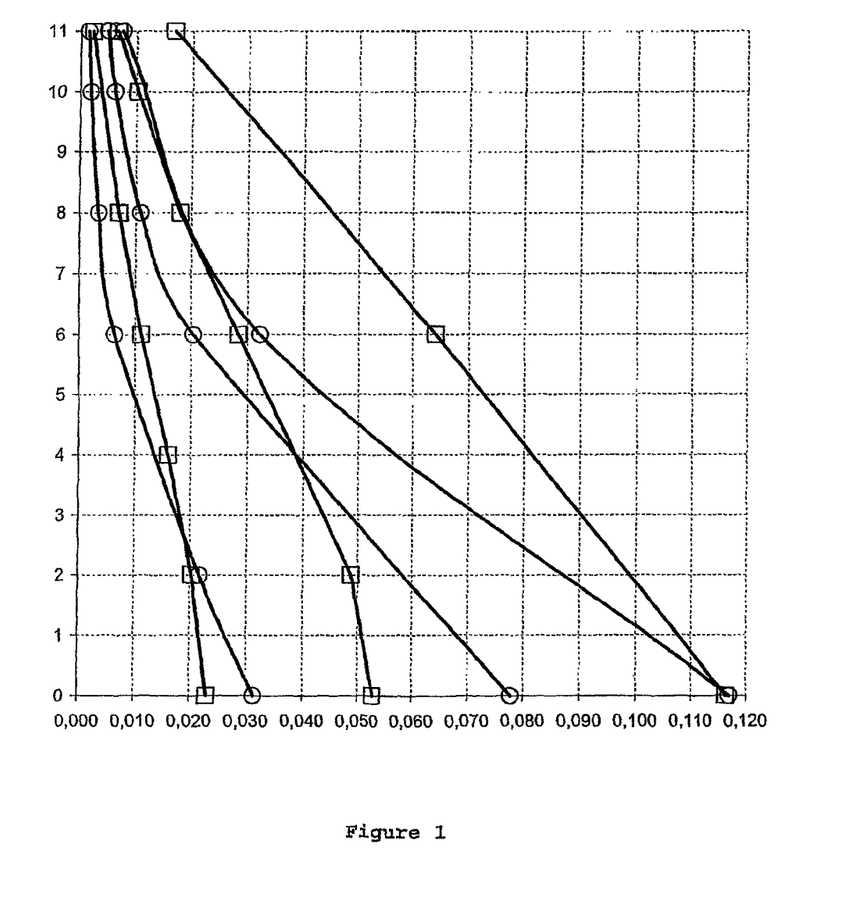

The methyl mercaptan concentration is measured by assay at the level of different trays down the column, and the results are presented in FIG. 1. The initial methyl mercaptan concentration (in %) in the gaseous mixture can be read from the figure at the level of "tray 0" and the final concentration after purification can be read at the level of "tray 11".

The results indicate that the absorbent solution according to the invention is more effective than the standard sulpholane-based absorbent solution for eliminating methyl mercaptan.

Example 2

Ability of an Absorbent Solution According to the Invention to Scrub Carbon Dioxide Pilot tests were carried out according to the same protocol as for Example 1, except that this time the absorbent solution flow rate is 610 kg/h, and that this time it is the $CO_2$ concentration which is measured at the level of different trays, in the case of a standard absorbent solution (DEA 40%+water 40%+sulpholane 20%) and in the case of an absorbent solution according to the invention (DEA 40%+water 40%+TDG 20%). In both cases, the initial gaseous mixture is composed of approximately 88% $N_2$ and 12% $CO_2$, 0 to 50 ppm $H_2S$ and approximately 670 ppm of methyl mercaptan.

Figure 2:
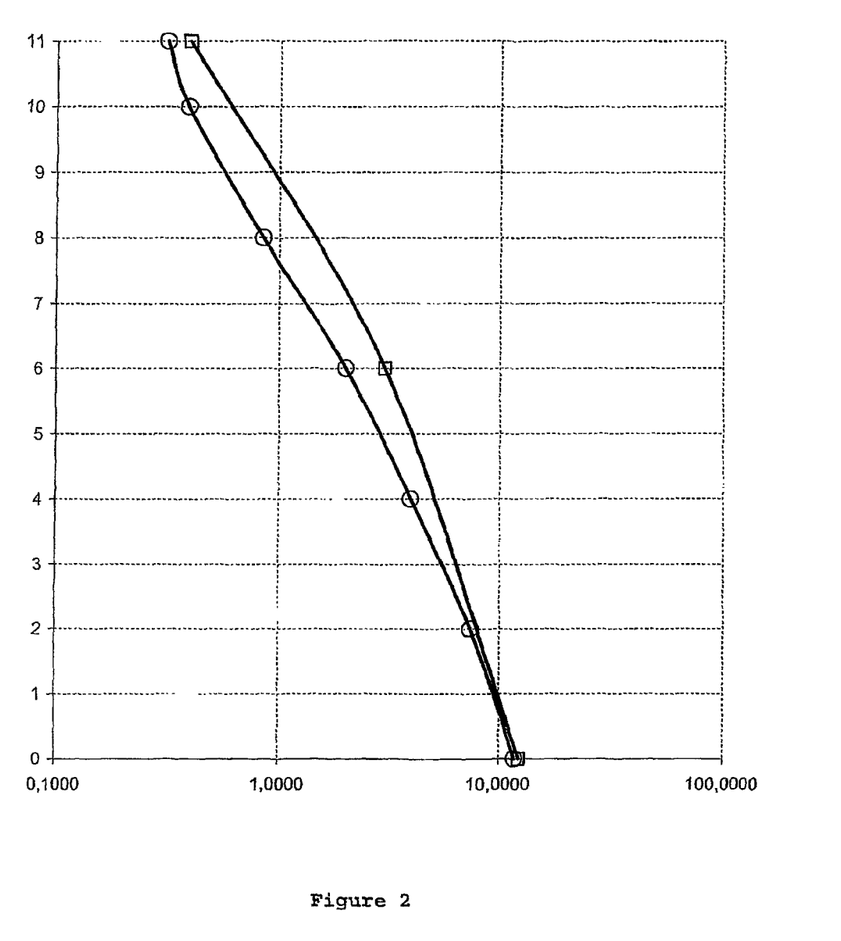
FIG. 2 represents the result of a comparative pilot test of the absorption of the carbon dioxide contained in a gaseous mixture (on a column), by an absorbent solution according to the invention on the one hand (diethanolamine 40%, water 40% and thiodiethylene glycol 20%; symbol ○) and by a standard absorbent solution on the other hand (diethanolamine 40%, water 40% and sulpholane 20%; symbol □). The percentage by volume of methyl mercaptan in the gaseous mixture is shown along the x-axis, and the number of plate trays passed through by the gaseous mixture in the column is shown along the y-axis.

The results, which are represented in FIG. 2, demonstrate a comparable effectiveness between the two absorbent solutions as regards the absorption of carbon dioxide.

The typical carbon dioxide absorption yields in pilot tests with the absorbent solution according to the invention are from 95 to 97%.

Example 3

Ability of an Absorbent Solution According to the Invention to Scrub Hydrogen Sulphide Pilot tests were carried out according to the same protocol as for Example 1, except that this time it is the $H_2S$ concentration which is measured after balancing the 11 plate trays. The gas flow rate is 200 kg/h, the liquid flow rate 1200 kg/h. The initial gaseous mixture, with a total pressure of 40 bar, contains $CO_2$ at a partial pressure of approximately 3 bar and $H_2S$ at a partial pressure of approximately 1 bar. The composition of the gaseous mixture is as follows: 90% $N_2$, 7.5% $CO_2$, 2.5% $H_2S$.

Figure 3:
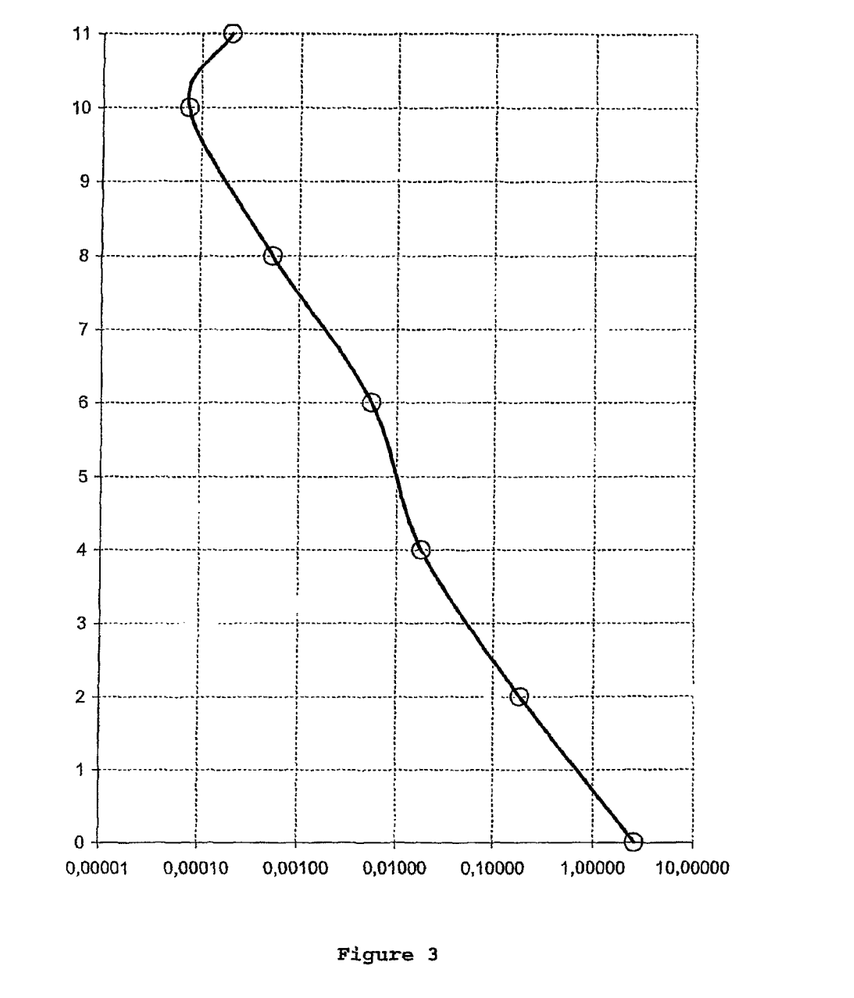
FIG. 3 represents the result of a pilot test of the absorption of the hydrogen sulphide contained in a gaseous mixture (on a column), by an absorbent solution according to the invention composed of diethanolamine (40%), water (40%) and thiodiethylene glycol (20%). The concentration by volume of $H_2S$ as a percentage is shown along the x-axis. The number of the plate tray in the column on which the measurement is carried out is indicated along the y-axis.

FIG. 3 represents the development of the hydrogen sulphide concentration during a treatment using an absorbent solution according to the invention (40% DEA+40% water+20% TDG). It appears that the performance of the absorbent solution according to the invention in this test is excellent. In eight plate trays the hydrogen sulphide concentration becomes less than 10 ppm, and reaches approximately 2 ppm on leaving the column. Thus, it can be considered that virtually all the hydrogen sulphide is eliminated from the gaseous mixture by means of the process of the invention.

Example 4

Ability of an Absorbent Solution According to the Invention to Scrub Carbonyl Sulphide Pilot tests were carried out according to the same protocol as for Example 1, except that this time it is the COS concentration which is measured after balancing the 11 plate trays. The gas flow rate is 215 kg/h, the liquid flow rate 1200 kg/h. The gas pressure is 40 bar. The solution used is composed of 40% DEA, 40% water and 20% TDG. The solvent moreover contains a residual concentration of dissolved $H_2S$ (of the order of 0.1% by mass).

Figure 4:
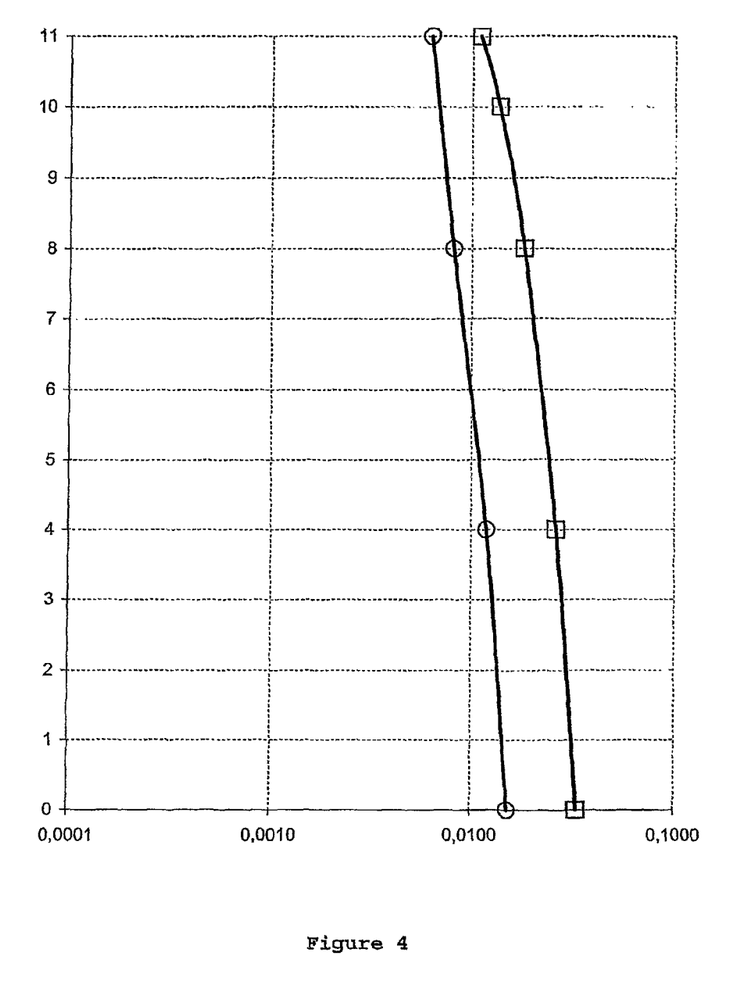
FIG. 4 represents the result of a pilot test of the absorption of the carbonyl sulphide contained in a gaseous mixture, by an absorbent solution according to the invention composed of diethanolamine (40%), water (40%) and thiodiethylene glycol (20%). The concentration by volume of COS as a percentage is shown along the x-axis. The number of the tray in the column on which the measurement is carried out is indicated along the y-axis.

Two tests were carried out. In the first one (□ curve), the partial pressure of $CO_2$ in the initial mixture (comprising mostly $N_2$) is 4.4 bar and that of COS is 330 ppm; in the second one (○ curve), the partial pressure of $CO_2$ in the initial mixture is 4.1 bar.

The results are shown in FIG. 4. It is noted that the absorption of COS is slower than for the other gases studied above. The final yield is equivalent to approximately 70% for the input at 330 ppm and approximately 60% for the input at 150 ppm.

Example 5

Comparison of the Absorption of Methyl Mercaptan at Equilibrium by Two Absorbent Solutions According to the Invention The absorption isotherm of methyl mercaptan by two absorbent solutions according to the invention was determined at 50° C., in the presence of CO2 at 500 mbar.

Experimental device: the absorbent solution was circulated in a 1.2 L double jacket reactor using a displacement pump. At the outlet of this pump, an exchanger is immersed in a thermostatic bath making it possible to maintain the reactor at a constant temperature, in order to compensate for the heat losses due to the passage of fluid in the pump. A Coriolis-effect mass flow meter continuously measures the density of the absorbent solution at the same temperature as that of the reactor. The introduction of the gaseous mixture is controlled by regulating mass flow meters, the pressure being kept constant by pressure adjustment. Circulation of the gases in the reactor is ensured by collecting them in the upper part and bubbling them into the absorbent solution using a disperser placed at the bottom of the latter. The whole gas circulation circuit, including the part leading to sampling by chromatography, is thermostatically controlled in order to avoid any condensation. The sampling output is recycled to the reactor in order to avoid modifying the pressure of the system.

Protocol: the absorbent solution is first introduced into the reactor. A certain quantity of gas is then introduced, followed by waiting for the pressure to stabilize, and if necessary a new quantity of gas is added until a stable final pressure is obtained. Nitrogen is optionally added in order to modify the partial pressure of the desired gas. Once equilibrium is reached, measurements are carried out, then the temperature of the system is modified by the thermostatically-controlled circuit in order to establish a new equilibrium.

Composition of the Two Tested Absorbent Solutions:
Solution No. 1: 40% DEA; 40% water; and 20% TDG.
Solution No. 2: 40% DEA; 40% water; and 20% methyl thioethanol ($CH_3$—S—$CH_2$—$CH_3$).

Figure 5:
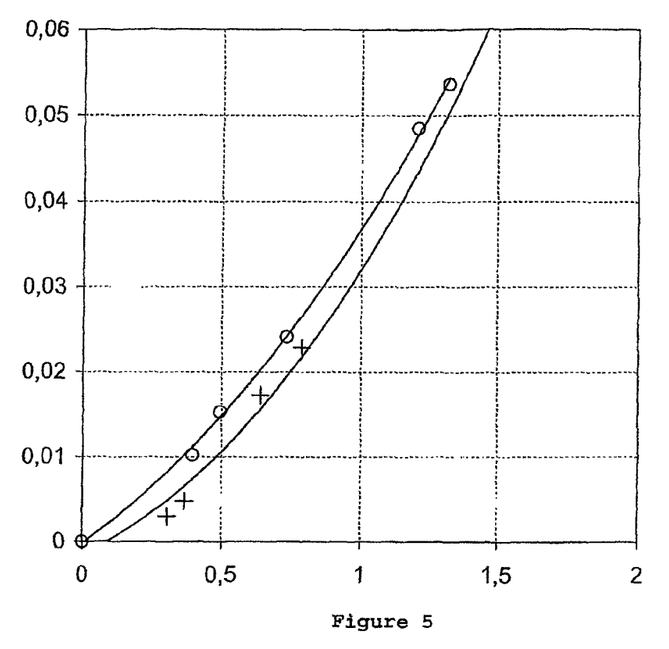
FIG. 5 represents the absorption isotherm of methyl mercaptan at 50° C. for two absorbent solutions according to the invention, namely on the one hand (+) a solution composed of 40% diethanolamine, 40% water and 20% thiodiethylene glycol, and on the other hand (○) a solution composed of 40% diethanolamine, 40% water and 20% methyl thioethanol. The quantity of methyl mercaptan in g per kg of loaded solution is shown along the x-axis, and the partial pressure of methyl mercaptan is shown along the y-axis.

The two solubility curves obtained are shown in FIG. 5. It should be noted that the two curves are close to each other, which indicates that the solution containing methyl thioethanol has methyl mercaptan absorption capacities similar to those of the solution containing TDG.

The invention claimed is:

1. Purification process for a gaseous mixture containing acid gases comprising a stage of bringing said gaseous mixture into contact with an absorbent solution comprising an alkanolamine, thiodiethylene glycol and water.

2. Purification process according to claim 1, in which the gaseous mixture comprises mercaptans and other acid gases.

3. Purification process according to claim 1 or 2 in which said gaseous mixture is natural gas.

4. Purification process according to claim 2 in which the mercaptan or mercaptans comprise methyl mercaptan and/or ethyl mercaptan.

5. Purification process according to claim 1, in which the acid gases comprise hydrogen sulphide and/or carbon dioxide and/or carbonyl sulphide.

6. Purification process according to claim 1 in which the alkanolamine is diethanolamine.

7. Purification process according to claim 1 in which the absorbent solution comprises:
20 to 60% by mass of diethanolamine;
20 to 60% by mass of water; and
10 to 40% by mass of thiodiethylene glycol.

8. Purification process according to claim 1 in which the absorbent solution comprises:
   30 to 45% by mass of diethanolamine;
   30 to 50% by mass of water; and
   15 to 30% by mass of thiodiethylene glycol.

9. Purification process according to claim 1 in which the absorbent solution comprises:
   40% by mass of diethanolamine;
   40% by mass of water; and
   20% by mass of thiodiethylene glycol.

10. Purification process according to claim 1 implemented in an absorber at a temperature comprised between 40 and 100° C.

11. Purification process according to claim 1 in which the gaseous mixture is brought into contact with the absorbent solution at a gaseous mixture flow rate comprised between $0.23 \ 10^6 \ Nm^3/day$ and $56 \ 10^6 \ Nm^3/day$ and at an absorbent solution flow rate comprised between $800 \ m^3/day$ and $50000 \ m^3/day$.

12. Purification process according to claim 1 also comprising a stage of regeneration of the absorbent solution loaded with mercaptans and other acid gases at a regeneration pressure comprised between 0 and 20 bar and at a temperature comprised between 100 and 140° C.

13. Purification process according to claim 1, for reducing the concentration of mercaptans contained in the gaseous mixture to a value of less than 5 µm.

14. Purification process according to claim 1 for reducing the concentration of hydrogen sulphide contained in the gaseous mixture to a value of less than 4 ppm.

15. Purification process according to claim 1 for reducing the concentration of carbon dioxide contained in the gaseous mixture to a value of less than 50 ppm.

16. Purification process according to claim 1 for reducing the concentration of carbonyl sulphide contained in the gaseous mixture to a value of less than 1 ppm.

17. Absorbent solution comprising:
   20 to 60% by mass of an alkanolamine;
   20 to 60% by mass of water; and
   10 to 40% by mass of thiodiethylene glycol.

18. Absorbent solution according to claim 17 comprising:
   30 to 45% by mass of an alkanolamine;
   30 to 50% by mass of water; and
   15 to 30% by mass of thiodiethylene glycol.

19. Absorbent solution according to claim 17 or 18, in which the alkanolamine is diethanolamine.

20. Purification process for a gaseous mixture containing acid gases comprising a stage of bringing said gaseous mixture into contact with an absorbent solution comprising an alkanolamine, ethylene dithioethanol and water.

21. Purification process according to claim 20, in which the gaseous mixture comprises mercaptans and other acid gases.

22. Purification process according to claim 20 or 21 in which said gaseous mixture is natural gas.

23. Purification process according to claim 22, in which the mercaptan or mercaptans comprise methyl mercaptan and/or ethyl mercaptan.

24. Purification process according to claim 20, in which the acid gases comprise hydrogen sulphide and/or carbon dioxide and/or carbonyl sulphide.

25. Purification process according to claim 20 in which the alkanolamine is diethanolamine.

26. Purification process according to claim 25 in which the absorbent solution comprises:
   20 to 60% by mass of diethanolamine;
   20 to 60% by mass of water; and
   10 to 40% by mass of ethylene dithioethanol.

27. Purification process according to claim 25 in which the absorbent solution comprises:
   30 to 45% by mass of diethanolamine;
   30 to 50% by mass of water; and
   15 to 30% by mass of ethylene dithioethanol.

28. Purification process according to claim 25 in which the absorbent solution comprises:
   40% by mass of diethanolamine;
   40% by mass of water; and
   20% by mass of ethylene dithioethanol.

29. Purification process according to claim 20 implemented in an absorber at a temperature comprised between 40 and 100° C.

30. Purification process according to claim 20 in which the gaseous mixture is brought into contact with the absorbent solution at a gaseous mixture flow rate comprised between $0.23 \ 10^6 \ Nm^3/day$ and $56 \ 10^6 \ Nm^3/day$ and at an absorbent solution flow rate comprised between $800 \ m^3/day$ and $50000 \ m^3/day$.

31. Purification process according to claim 20 also comprising a stage of regeneration of the absorbent solution loaded with mercaptans and other acid gases at a regeneration pressure comprised between 0 and 20 bar and at a temperature comprised between 100 and 140° C.

32. Purification process according to claim 20, for reducing the concentration of mercaptans contained in the gaseous mixture to a value of less than 5 ppm.

33. Purification process according to claim 20 for reducing the concentration of hydrogen sulphide contained in the gaseous mixture to a value of less than 4 ppm.

34. Purification process according to claim 20 for reducing the concentration of carbon dioxide contained in the gaseous mixture to a value of less than 50 ppm.

35. Purification process according to claim 20 for reducing the concentration of carbonyl sulphide contained in the gaseous mixture to a value of less than 1 ppm.

36. Absorbent solution comprising:
   20 to 60% by mass of an alkanolamine;
   20 to 60% by mass of water; and
   10 to 40% by mass of ethylene dithioethanol.

37. Absorbent solution according to claim 36 comprising:
   30 to 45% by mass of an alkanolamine;
   30 to 50% by mass of water; and
   15 to 30% by mass of ethylene dithioethanol.

38. Absorbent solution according to claim 36 or 37, in which the alkanolamine is diethanolamine.

* * * * *